US00PP32987P2

(12) United States Plant Patent
Horvath et al.

(10) Patent No.: US PP32,987 P2
(45) Date of Patent: Apr. 20, 2021

(54) ***DIANTHUS* HYBRID PLANT NAMED 'FUCHSIA FIRE'**

(50) Latin Name: ***Dianthus* hybrid**
Varietal Denomination: Fuchsia Fire

(71) Applicants: Brent Arpad Horvath, Fontana, WI (US); Jacob R. Letmanski, McHenry, IL (US)

(72) Inventors: Brent Arpad Horvath, Fontana, WI (US); Jacob R. Letmanski, McHenry, IL (US)

( * ) Notice: Subject to any disclaimer, the term of this patent is extended or adjusted under 35 U.S.C. 154(b) by 0 days.

(21) Appl. No.: 16/873,628

(22) Filed: May 26, 2020

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./272, 273, 277
See application file for complete search history.

*Primary Examiner* — Susan McCormick Ewoldt

(57) ABSTRACT

A new, distinct *Dianthus* plant as illustrated and described, characterized by magenta pink flowers on short stems, above mat forming and compact silvered foliage.

1 Drawing Sheet

Figure 1:
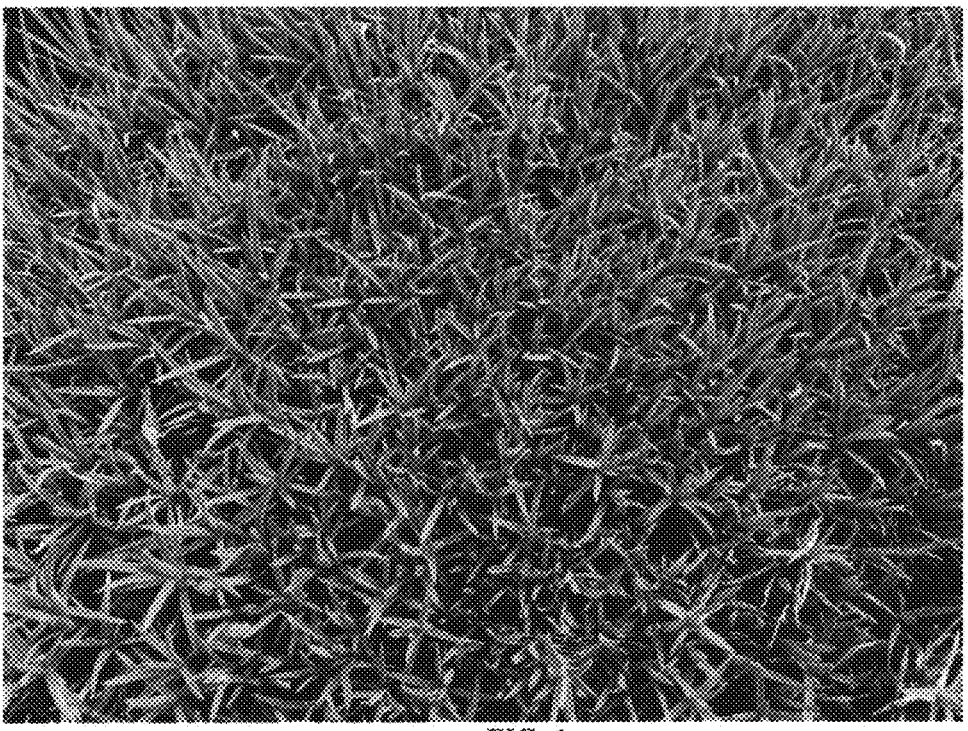

Latin name: *Dianthus* hybrid.
Cultivar name: 'Fuchsia Fire'.

BACKGROUND OF THE INVENTION

The present invention relates to a new and distinct plant of *Dianthus* hybrid plant named 'Fuchsia Fire' characterized by magenta pink flowers on short stems, above mat forming and compact silvered foliage. The new *Dianthus* was the result of an intentional cross by the inventors at a nursery, in Hebron, Ill. in 2017. The selection of the new plant was due to its' magenta pink flowers on short stems, above mat forming and compact silvered foliage, compared to the taller stems and mounding foliage of the parent plants. Initial asexual reproduction has taken place at a nursery in Hebron, Ill. since 2018 by means of vegetative tip cuttings. The new *Dianthus* has shown to be stable and identical in reproduction after rooting over 700 plants from 2018 to 2019.

No plants of the new *Dianthus* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Dianthus* hybrid plant named 'Fuchsia Fire' characterized by magenta pink flowers on short stems, above mat forming and compact silvered foliage, have been observed to be unique and stable.

Plants of the new *Dianthus* hybrid plant named 'Fuchsia Fire' can be compared to the female or seed parent *Dianthus gratianopolitanus* 'Firewitch', not patented. 1. The new *Dianthus* plant has flower stems measuring 12-15 cm long compared to the stems of 'Firewitch' which measure 20 cm or longer. 2. The new *Dianthus* also has smaller foliage on shorter growing plants reaching only 7 cm tall while 'Firewitch reaches 15-20 cm tall.

Plants of the new *Dianthus* can be compared to plants of the male or pollen parent *Dianthus* 'Paint the town Fuchsia' patented, U.S. Plant Pat. No. 28,636. 1. The new *Dianthus* plant has silvered foliage RHS color 147 B while *Dianthus* 'Paint the town Fuchsia' plant has a foliage color 137 B. 2. The new *Dianthus* plant has flower colors RHS color N74 A while *Dianthus* 'Paint the town Fuchsia' plant has flower colors of N78 A. 3. The new *Dianthus* plant has a foliage height of 7 cm and flower stems 10-12 cm in length while *Dianthus* 'Paint the town Fuchsia' plant has a foliage height of 12 cm and flower stems 20 cm in length.

Plants of the new *Dianthus* can be compared to plants of *Dianthus gratianopolitanus* 'Grandiflorus' not patented. 1. The new *Dianthus* plant has flower colors RHS color N74 A while *Dianthus gratianopolitanus* 'Grandiflorus' plant has bi-color pink flowers with a darker near red colored eye. 2. The new *Dianthus* plant has flower stems 10-12 cm in length while *Dianthus gratianopolitanus* 'Grandiflorus' plant has flower stems 20 cm in length. 3. The new *Dianthus* plant has flowers 28 mm in width while *Dianthus gratianopolitanus* 'Grandiflorus' plant has flowers nearly 40 mm in width.

DESCRIPTION OF PHOTOGRAPHS

Figure 2:
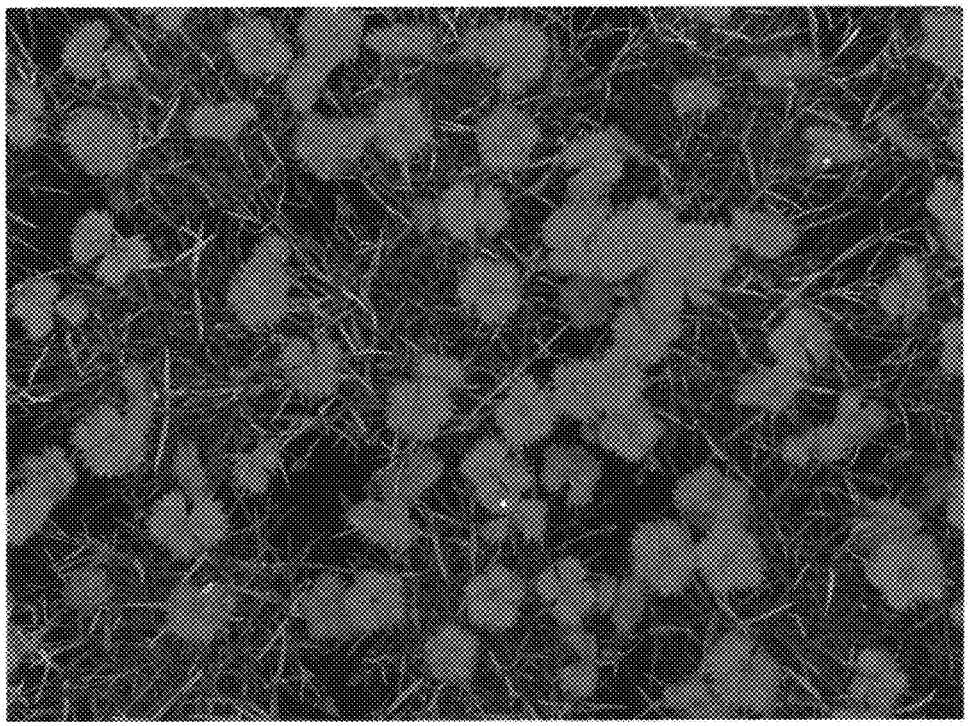

Plants pictured in the drawing were grown for one year.
FIG. 1. Close up of the foliage.
FIG. 2. A picture of many plants blooming together.

DETAILED BOTANICAL DESCRIPTION

In the following description, color references are made to The Royal Horticultural Society Colour Chart (2001). Plants used for the description were grown for one year. Measurements and numerical values represent averages of typical plants.

Botanical classification: *Dianthus* hybrid plant named 'Fuchsia Fire'.

Parentage: Female or seed parent *Dianthus gratianopolitanus* 'Firewitch', male or pollen parent *Dianthus* 'Paint the town Fuchsia' patented, U.S. Plant Pat. No. 28,636.

Propagation: Vegetative tip cutting propagation.

Plant description: Overall habit of the new *Dianthus* is mat forming clumps to 7 cm tall and 40 cm wide, with up to 15 cm stems topped by magenta pink flowers May through June.

*Plant height*.—Average 7 cm.

*Plant width*.—40 cm.

*Growth habit*.—Moderately vigorous.

Stems: Upright, terete, branching at alternate nodes, around 70 per plant.

*Stem color*.—138 B in spring, summer, and fall.

*Stem shape*.—Both typical and observed — round.

*Stem texture*.—Glabrous, glaucous.

*Stem length*.—3 cm, Stem diameter — 3 mm.

*Stem branching*.—Numerous, typically alternate from lower leaf axils, about 2-3 per main stem, branch length 5 cm at the time of flowering.

*Nodes*.—About 3-4 per stem.

*Internode length*.—5 mm.

*Roots*.—Fine, fibrous, color close to 159A.

Foliage:

*Type*.—Simple, linear, opposite, decussate, sessile, glabrous, glaucous on adaxial and abaxial sides.

*Leaf division*.—Simple.

*Leaf attachment*.—Sessile.

*Shape*.—Linear.

*Petiole*.—None.

*Length*.—4-5 cm.

*Width*.—2-3 mm.

*Thickness*.—3 mm.

*Margin*.—Entire.

*Leaf apex, typical and observed*.—Acute.

*Leaf bases, typical and observed*.—Decurrent.

*Texture*.—Glabrous and glaucous.

*Leaf arrangement*.—Opposite, crowded.

*Leaf venation pattern*.—None.

*Leaf vein color*.—None.

*Adaxial leaf description*.—Color is 137 B.

*Abaxial leaf description*.—Color is 147 B.

*Fall foliage color*.—None noticed.

Flower:

*Type*.—Terminal, cymose.

*Aspect*.—Upright.

*Inflorescence type*.—Perfect, single.

*Inflorescence size*.—28 mm across.

*Flower number*.—2 per stem, 140 per plant.

*Flower longevity*.—Five days.

*Flower fragrance*.—Medium, spice like.

*Bloom period and duration*.—Late spring; sporadically to early fall.

*Blooming habit*.—Solitary on up to 15 cm stems.

*Petal count*.—5.

*Petal texture*.—Glabrous.

*Petal arrangement*.—Rotate.

*Petal shape*.—Obovate.

*Adaxial petal color*.—N74 A.

*Abaxial petal color*.—N74 B.

*Petal apex shape*.—Obovate.

*Petal bases, typical and observed*.—Acute, 20 mm wide.

*Petal length*.—Up to 28 mm, Petal width — 14 mm.

*Petal margin, typical and observed*.—Dentate up to 3 mm deep a 2 mm wide.

*Bud length, typical and observed*.—2 cm.

*Bud diameter, typical and observed*.—5 cm.

*Bud color, typical and observed*.—N74 A.

*Sepal size*.—2 mm across, 6 mm tall, Sepal number — 5.

*Sepal shape, typical and observed*.—Lanceolate.

*Sepal apex, typical and observed*.—Acute.

*Sepal base, typical and observed*.—Acute.

*Sepal margin, typical and observed*.—Entire.

*Sepal surface, typical and observed*.—Smooth.

*Sepal color, abaxial and adaxial typical and observed*.—146 C.

*Peduncle*.—Glabrous, glaucous, terete.

*Pedicle color, typical and observed*.—Close to 138 B.

*Pedicle length, typical and observed*.—3 cm.

*Pedicle diameter, typical and observed*.—1 mm.

*Pedicle color, typical and observed*.—Close to 138 B.

*Pedicle surface, typical and observed*.—Glaucous, glabrous, terete.

*Bracts*.—Two pair, opposite, glaucous, glabrous, sessile, margin entire, broadly obtuse with acute apex; outer pair 3 mm long and 3 mm wide; inner pair 7 mm long and 3 mm wide.

*Bract color*.—Abaxial and adaxial typical and observed — 137 A and B.

*Androecium*.—Absent.

*Stamens*.—Absent.

*Anthers*.—Absent.

*Pollen color*.—Absent.

*Gynoecium*.—

*Style*.—Split in two above the ovary.

*Pistil*.—Glabrous abaxial and adaxial surface, curled in distal 4 mm.

*Pistil length*.—15 mm, shape — slender, 1 mm diameter, Color N155 B.

*Stigma*.—Glabrous, about 0.5 mm long and 0.5 mm wide. Color 79 C.

*Ovary*.—Superior, ellipsoid shaped, size — 8 mm long and 3 mm wide, Color close to 145 B and 150 D.

*Fertility*.—None observed.

*Fruit*.—Capsule, oblong ovoid with rounded base and acute apex, opening buy 4 teeth, 3 mm long and 2 mm diameter, color 164 C.

*Seed*.—None observed.

*Hardiness*.—U.S.D.A. hardiness zones 5-10.

*Disease resistance*.—Resistance to diseases common to *Dianthus* has not been observed on plants grown under nursery conditions.

*Pest resistance*.—Resistance to pests common to *Dianthus* has not been observed on plants grown under nursery conditions.

We claim:

1. A new, distinct *Dianthus* plant as illustrated and described, characterized by magenta pink flowers on short stems, above mat forming and compact silvered foliage.

* * * * *